(12) United States Patent
Ochs

(10) Patent No.: US 8,239,014 B2
(45) Date of Patent: Aug. 7, 2012

(54) SEQUENTIAL LOW ENERGY NEUROFEEDBACK TREATMENT

(75) Inventor: Len Ochs, Sebastapol, CA (US)

(73) Assignee: Ochslabs, Inc., Sebastopol, CA (US)

( * ) Notice: Subject to any disclaimer, the term of this patent is extended or adjusted under 35 U.S.C. 154(b) by 0 days.

(21) Appl. No.: 13/101,321

(22) Filed: May 5, 2011

(65) Prior Publication Data

US 2011/0282234 A1  Nov. 17, 2011

Related U.S. Application Data

(60) Provisional application No. 61/333,837, filed on May 12, 2010.

(51) Int. Cl.
*A61B 5/04* (2006.01)

(52) U.S. Cl. ....................................................... 600/544

(58) Field of Classification Search ........... 600/544–545
See application file for complete search history.

(56) References Cited

U.S. PATENT DOCUMENTS

| 5,036,858 A | 8/1991 | Carter et al. |
|---|---|---|
| 5,365,939 A | 11/1994 | Ochs |
| RE36,348 E | 10/1999 | Carter |
| 7,035,686 B2 | 4/2006 | Hogan |
| 2003/0144601 A1* | 7/2003 | Prichep .................. 600/544 |
| 2003/0225340 A1 | 12/2003 | Collura |
| 2004/0002635 A1* | 1/2004 | Hargrove et al. ............ 600/300 |
| 2006/0258950 A1 | 11/2006 | Hurgrove et al. |
| 2008/0082020 A1 | 4/2008 | Collura |
| 2009/0281447 A1 | 11/2009 | Gerdes |

* cited by examiner

*Primary Examiner* — Michael Kahelin
*Assistant Examiner* — Christian Jang
(74) *Attorney, Agent, or Firm* — Edward S. Sherman (57) ABSTRACT

The dominant brain wave frequencies of a patient are measured by an electroencephalogram (EEG) with a plurality of leads over the head and scalp. In a process for low energy neuro-feedback, the therapeutically beneficial low power RF field is sequentially applied via the same at a different frequency, which is generally offset from the dominant frequency by 5 to 20 Hz. The order of applying these low power stimuli to the different leads is optimized based on the activity observed at each lead and its variation over time. Leads positions having a greater Coefficient of Variation are treated first.

20 Claims, 8 Drawing Sheets

SEQUENTIAL LOW ENERGY NEUROFEEDBACK TREATMENT

CROSS REFERENCE TO RELATED APPLICATIONS

The present application claims the benefit of priority to the US provisional patent application of the same title having Ser. No. 61/333,837 that was filed on May 12, 2010, which is incorporated herein by reference

BACKGROUND OF INVENTION

The present invention relates to an apparatus and method of brain therapy using low energy neurofeedback, and in particular to an improved sequence for providing such neurofeedback at different locations on the scalp.

Generally speaking, neurofeedback is a method of treating physical or psychological disorders having some form of organic brain dysfunction. Various methodologies involve recording the brain electrical activity from pattern of electrical leads placed on and around the scalp, known as an electroencephalograph or EEG.

The EEG reveals periodic variations in electrical activity within the brain, which has traditionally been characterized as combinations of four frequency bands or components; which are delta, theta, alpha, and beta. While the state of consciousness is the primary cause of one frequency being dominant over the other, subtle variations in these components frequently indicate underlying disorders. During sleep, delta waves having a frequency of four hertz (Hz) are dominant. Theta waves (4 to 8 Hz) are associated with the twilight consciousness on the brink of sleep, during which dreamlike mental images can surface. At higher frequency still are alpha (8 to 12 Hz), which are dominant in the calm and mentally unfocused state typically connected with relaxation. Beta waves, from 12 to 35 Hz are dominant in the normal waking state, when our eyes are open and focused on the world. When the patient is relaxed but alert the beta waves tend to be at the lower frequency range of 12 to 15 Hz, whereas in the excited, anxious state the beta waves can be as high as 35 Hz. Early EEG neurofeedback using an operant conditioning model focused on helping people learn to generate waves associated with deep relaxation: alpha and theta. Other treatment modalities evolved in which the patient received a stimulus based on the results of the EEG.

Although neurofeedback modifies the brain function in a manner not fully understood, such treatments are now well correlated with therapeutic benefits for many types of disorders. Further, changes in a patient's EEG can also reveals that the brain function is modified by the feedback.

One such method is more fully described in U.S. Pat. No. 5,365,939 (issued to Ochs on No. 22, 1994), and U.S. Pat. No. 5,036,858 (issued to Carter et al. on Aug. 6, 1991 and reissued as RE 36,348 on Oct. 19, 1999), both of which are incorporated herein by reference. The feedback to the patient is via goggles that contain light emitting diodes (LEDs), but may also include sounds. The treatment, via the output of LED's, was accomplished at two different frequencies, but always within a predetermined range of the current actual brain wave frequency and the desired frequency. The apparatus to accomplish this method had a computer processor, a computer memory, EEG electrodes along with an amplifier, a programmable timing generator responsive to the computer processor for generating the two frequencies, audio amplifiers and a beat frequency generator driving a visual frequency amplifier.

It was subsequently discovered that the patient did not need to actually see the LEDs in the goggles for the therapy to have a benefit. The LEDs could be masked or completely blocked and the patient would still show clinical improvement. It was surprisingly discovered that very low intensity electric fields generated by the current to the LEDs in the goggles was therapeutically effective.

Figure 2A:
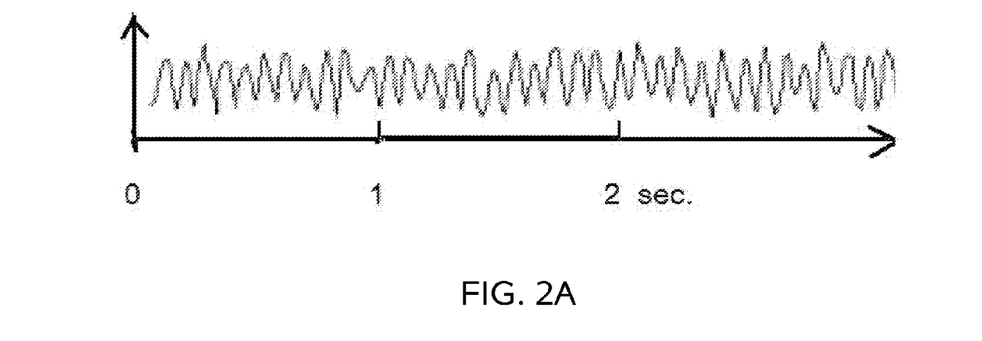
Figure 2B:
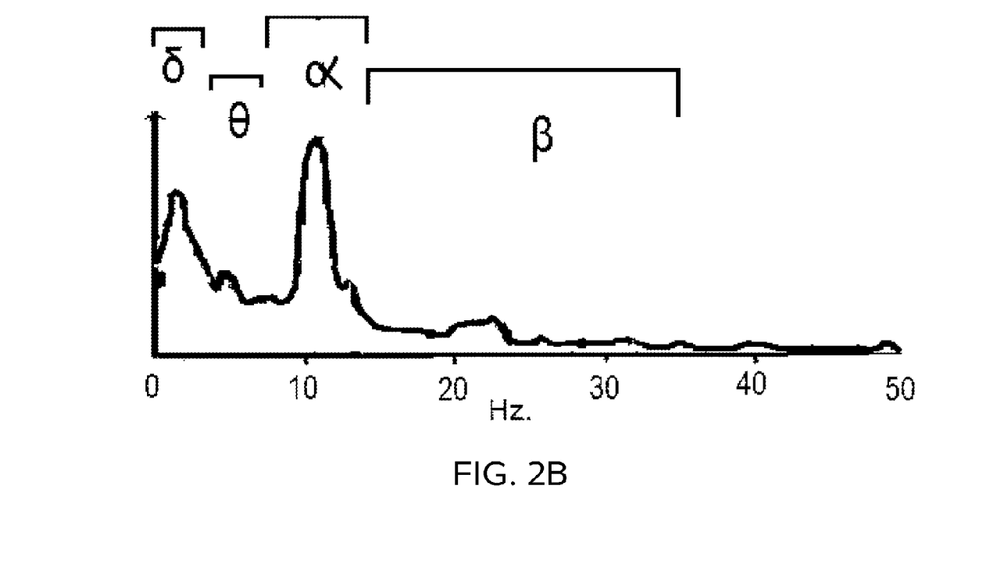
FIG. 2B is an exemplary power spectrum derived by a FFT of a time domain EEG signal such as that in FIG. 2A.

This discovery then led to the state of the art Low Energy Neurofeedback System, or LENS, of which an exemplary system for such treatment is shown in FIG. 2. The LENS method employs extremely weak intensities of feedback and does involve the patient's own EEG driving the feedback, but does not involve any conscious participation or even positive intention. The LENS method works by continuously monitoring EEG activity and then uses these readings to determine the frequency of very small electromagnetic fields that are "offset" several cycles per second (hertz) faster than the patient's dominant brainwave frequency. LENS uses an electromagnetic field as the carrier wave for the feedback. With this method, the EEG leads serve as bi-directional conduits for both the brainwaves and the feedback signals. This feedback stimulus input is then delivered down electrode wires at generally seven or fewer electrode sites in the course of a treatment session, typically for only one second per site. This input is much weaker than what the brain receives from holding a cell phone to one's ear, the power being in the range of nano-watts/cm2. The LENS approach is reviewed in the Journal of Neurotherapy, Vol 10, no. 2/3, 2006, pp. 5-39, which is incorporated herein by reference.

In the LENS method either the computer or a microprocessor associated with EEG amplifier performs the calculations based on the EEG and then delivers power to different leads placed on the patient's scalp. The exact order of treatment, power, duration and like parameters depends on the clinical findings, and in particular an initial evaluation of the patient's sensitivity to treatment.

Figure 1:
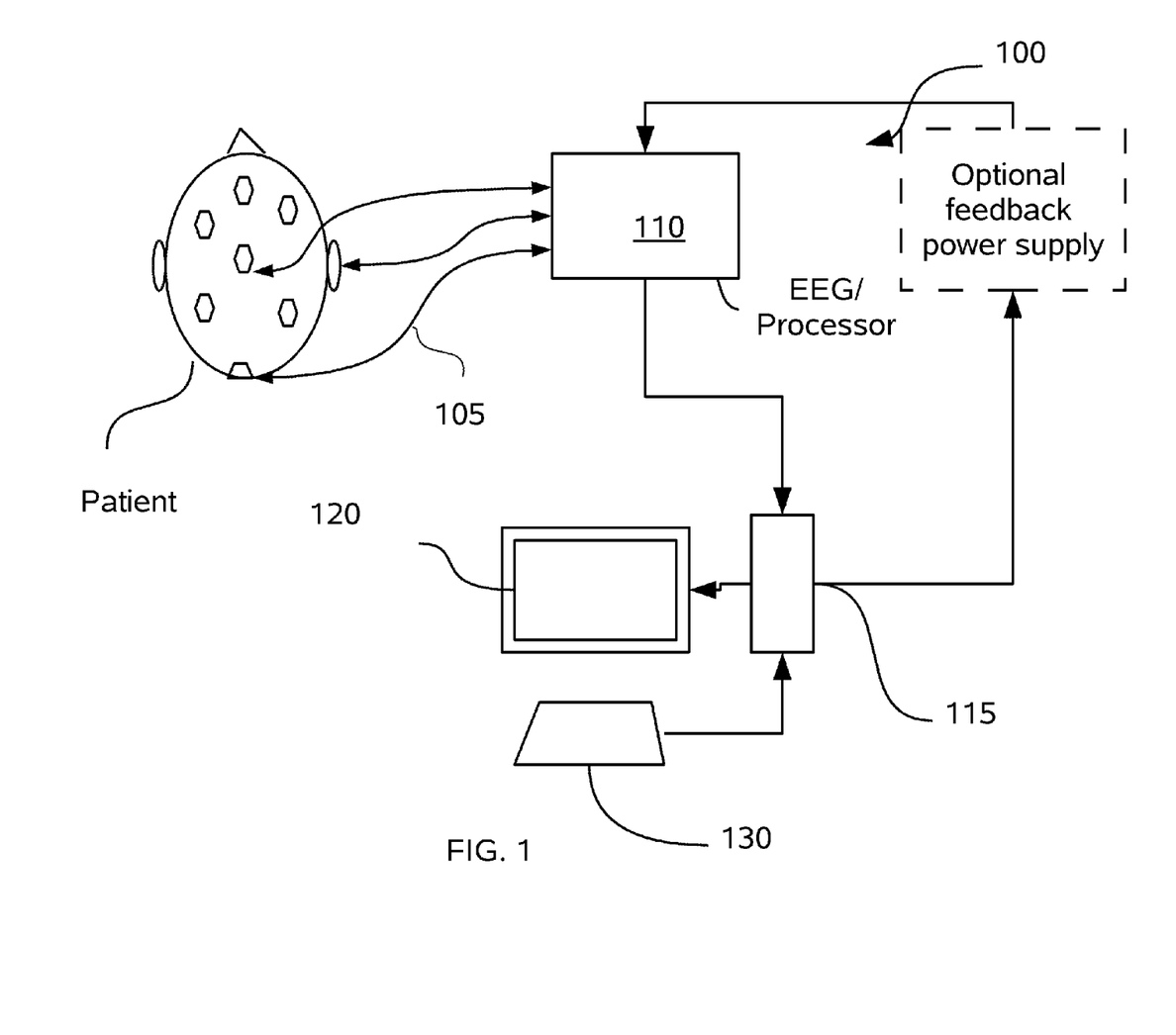
FIG. 1 is a schematic illustration of the LENS system that uses an EEG leads and an EEG amplifier that is connected to a general purpose computer as is optionally used to treat individuals in the inventive method of neurofeedback.

A block diagram of the LENS system is shown in FIG. 1. The EEG amplifier/microprocessor 110 that is used to acquire the EEG and provide the feedback stimulus may be acquired from J&J Engineering Incorporated, 22797 Holgar Ct. NE, Poulsbo, Wash. 98370, subject to restrictions customary for medical devices. The software that interfaces with the EEG acquisition system of J & J Engineering for the LENS method is available from OchsLabs, 6683 Sebastopol Avenue., Sebastopol, Calif. 95472, subject to similar restrictions. The software aids in the clinician's diagnosis, treatment plan development and actual treatment based on the LENS protocols, which vary depending on the patient's condition and the reason for treatment, among other factors.

It is a primary object of the present invention to provide an improvement in the efficiency of the LENS treatment.

SUMMARY OF INVENTION

In the present invention, the first object is achieved by providing a method of low energy neurofeedback treatment, the method comprising the steps of attaching a plurality of EEG leads to the head of a the patient, acquiring a baseline EEG at 2 or more leads of said plurality, calculating the FFT of the acquired baselines for at least 16 time segments, calculating a COV from the FFT for each of the 2 or more leads in said plurality, providing a neurofeedback treatment to the patients via at least some of the each of the 2 or more leads in said plurality, the neurofeedback being provided in the sequence of EEG leads characterized by a higher COV to lower COV.

A second aspect of the invention is characterized by the aforementioned method for low energy neurofeedback treatment, the method further comprising the step of calculating a COV for 2 or more activity parameters for each of the 2 or more leads in said plurality, and selecting one of said activity parameters for the purpose of providing the neurofeedback in the order of highest COV to lowest COV of said selected activity parameter.

Yet another aspect of the invention is characterized by the aforementioned method for low energy neurofeedback treatment is selecting the activity parameter having the greater number of EEG sites that meet a predetermined selection criteria.

More specifically, these objects are achieved by measuring the patient's EEG at each of the standard International 10-20 electrode sites as a way to gather data to generate a topographic surface EEG map. This is achieved by providing a method of low energy neurofeedback treatment, the method comprising the steps of attaching a plurality of EEG leads to the scalp of a the patient, acquiring EEG measurements from at 2 or more leads of said plurality, calculating the FFT of the acquired baselines for at least 16 time segments per second, for at least two seconds at each sensor site, and from that deriving a peak, or dominant frequency. From this data is calculated for each band, e.g., delta, theta, alpha, low beta, beta, high beta, and total amplitudes as well as the peak or dominant frequency at each sensor site. From this data in each site, each EEG band, for both amplitude and peak frequency is calculated a COV from the FFT for each of the 2 or more leads in said plurality The above and other objects, effects, features, and advantages of the present invention will become more apparent from the following description of the embodiments thereof taken in conjunction with the accompanying drawings.

BRIEF DESCRIPTION OF THE DRAWINGS

FIG. 2A is a typical graph of power versus time that might be obtained from one EEG electrode and thus illustrates an EEG in time domain, whereas

FIG. 3A is a schematic illustration of electrode placement in elevation view from the left side of patients head corresponding to the 10-20 International System, whereas

DETAILED DESCRIPTION

Referring to FIGS. 1 through 6, wherein like reference numerals refer to like components in the various views, there is illustrated therein a new and improved neurofeedback method.

Figure 4A:
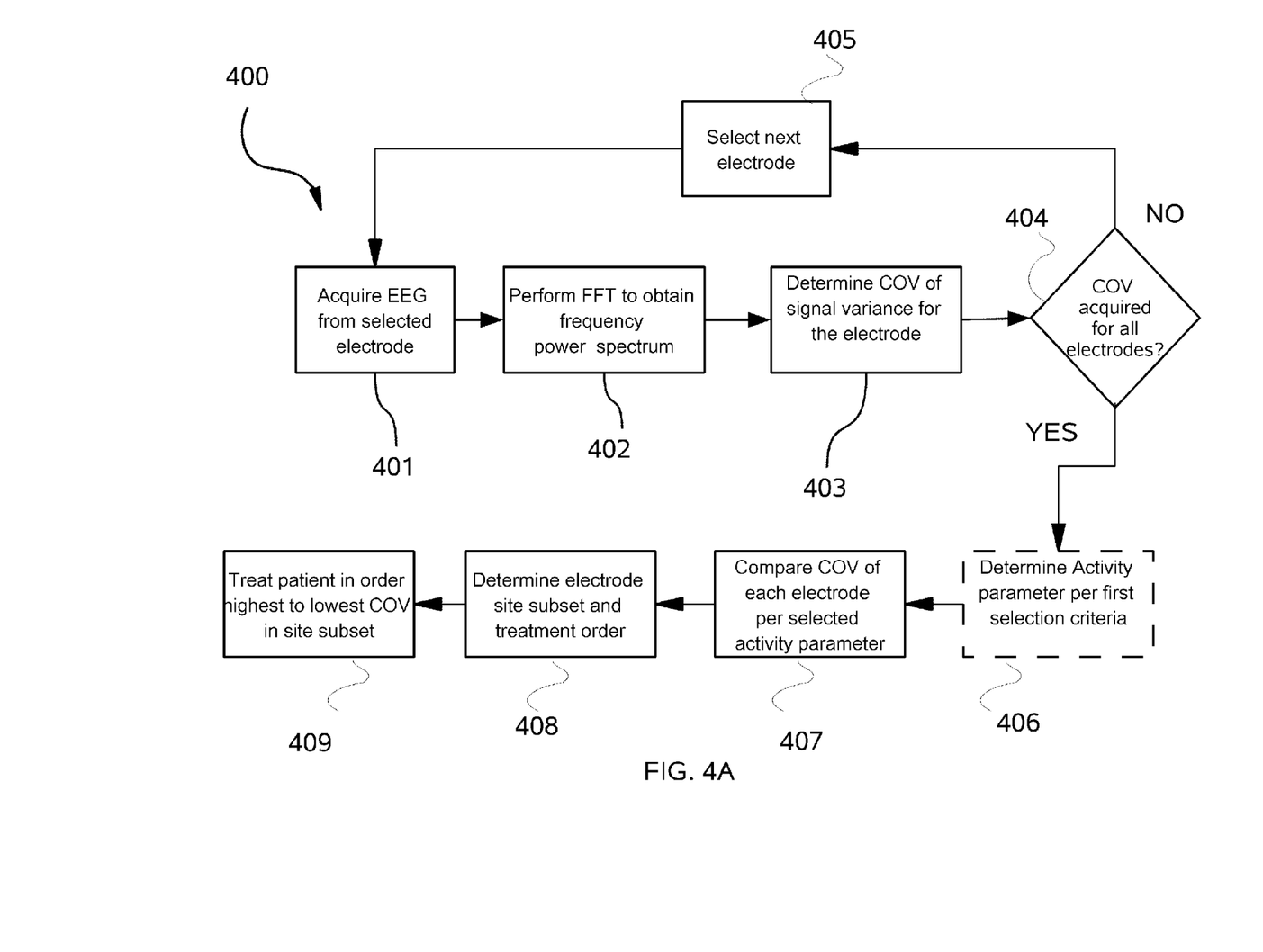
FIG. 4A is a flow chart for the inventive treatment process that deploys the apparatus of FIG. 1.

The present invention is primarily concerned with an improvement to the LENS methods wherein it has been discovered that an effective treatment can be predicted based on a clinical evaluation of the patient's brain activity. More particularly, the improvement arises from the order in which treatment is provided at each EEG lead. One such treatment method is disclosed in the co-pending US patent application for a "Neurofeedback System" having Ser. No. 12/535,074, which was filed on Aug. 4, 2009, and published on Feb. 11, 2010 under US Publication No. US-2010-0036276-A1, which is incorporated herein by reference. This application disclosed that the unamplified feedback from the computer or the digital signal processor (DSP) in an EEG amplifier via the EEG leads can be therapeutically effective. Thus in some clinical conditions either the unamplified feedback from the computer or amplified or unamplified feedback from the EEG amplifier may be deployed in step 409 of the process 400, as shown in FIG. 4A.

It should be understood that the functions of the EEG amplifier and the general purpose computer can also be integrated into one device, as for example by configuring the EEG amplifier 110 as a card that plugs into the backplane of the general purpose computer 115 or another port, as well as providing an appropriate computer microprocessor or DSP in the same box as the EEG amplifier 110.

The present invention is particularly concerned with an improvement to the treatment method 400 wherein the order of treatment at select electrodes 105 is determined by the variation in electrical activity at each electrode prior to the treatment process 400.

Figure 3A:
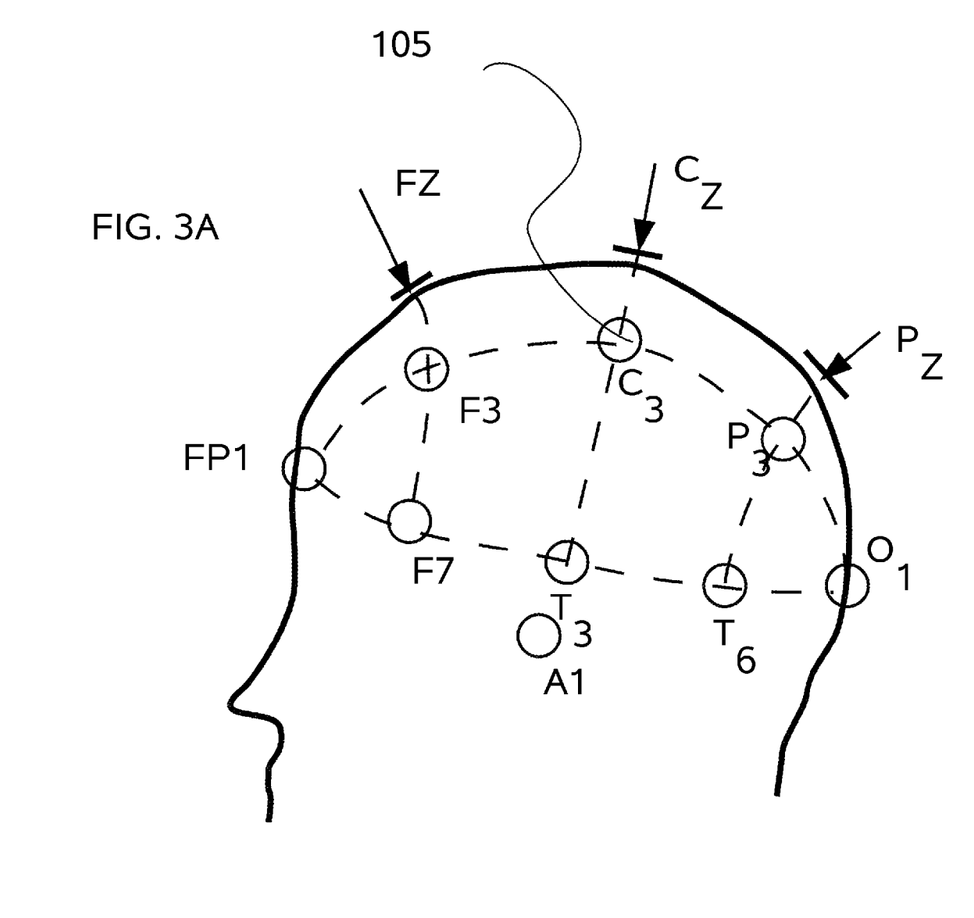
Figure 3B:
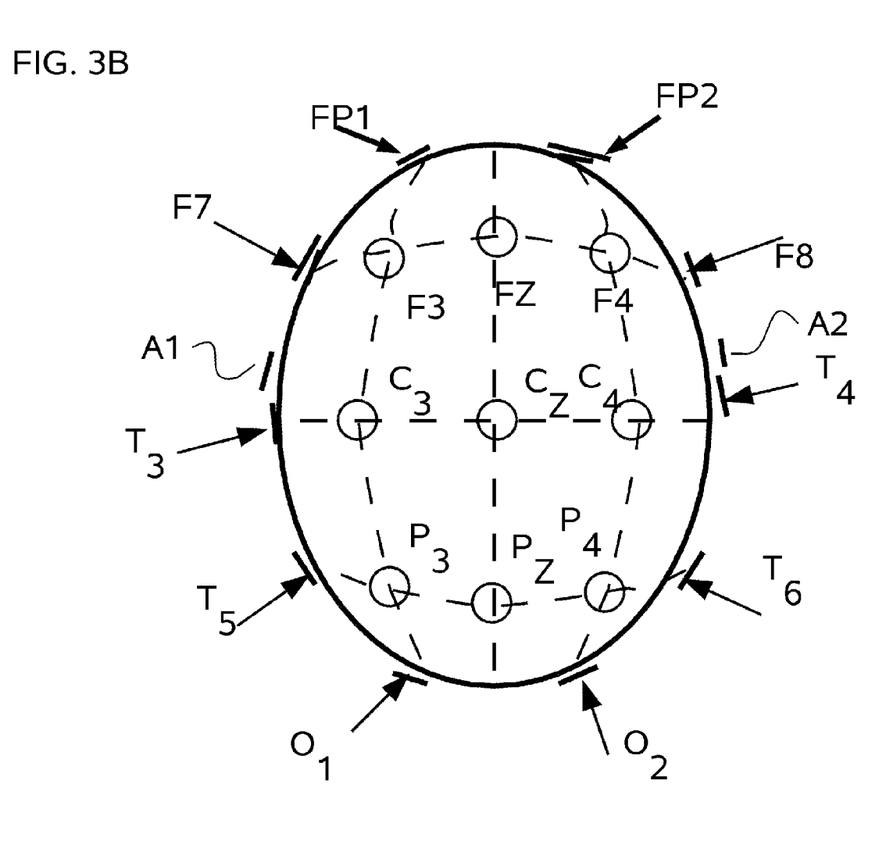
FIG. 3B is the plan view thereof.

In accordance with the present invention, FIG. 1 is a schematic illustration of an apparatus for LENS treatment which can deploy the inventive method 400. The system comprises a plurality of EEG leads 105 connected to the patient, such as shown in FIG. 3A and FIG. 3B, and optionally a feedback power supply in signal communication with the EEG leads 105 via the EEG/processor amplifier 110 through the general purpose computer 115 in signal communication therewith.

The EEG/processor amplifier 110 may provide the general purpose computer 115 with amplified analog signals provided the computer also has an A/D converter, or the A/D converter may reside in the EEG/processor amplifier. It should be appreciated that the EEG amplifier 110 serves to collect the relatively weak EEG signals via the leads and amplify them sufficiently for analysis by the general purpose computer 115. Such commercial EEG amplifiers may include A/D converters and generally also have the means to perform a Fast Fourier Transform (FFT) to convert the time domain EEG to a frequency domain resulting in a power spectrum. Furthermore, such commercial instruments also generally will provide at least one of the instantaneous or time average integral of amplitude or power over each of the characteristic wavelengths; delta, theta, alpha, low beta, beta, high beta and total. Thus, such commercial EEG's amplifiers are also generally sold with software for use with a general purpose computer for the display, analysis and manipulation of the EEG spectral data. Therefore, such a general purpose computer 115 also comprises a display 120, which preferably deploys a graphic user interface and a key board 130 or equivalent user interface so that the user can control the computer 115 and the course of treatment, as is determined from the patient EEG spectral analysis.

Thus, a typical EEG spectrum, as received and optionally displayed at the general purpose computer 120 in time domain is shown in FIG. 2A. FIG. 2B is a typical power spectrum obtained by an FFT of the signal in FIG. 2A showing various peaks in the frequency bands known as alpha, beta, theta and delta and total, often indicated by the corresponding Greek letter above the spectrum.

It should be appreciated that while FIG. 1 only shows a single EEG lead 105 connected to the patient, in most clinical EEG mapping applications 21 leads are connected to different portions of the scalp to both acquire signal to generate topographic EEG maps. While providing EEG feedback it is customary for between 1 and 4 sets of leads to be connected to the patient. Preferably, the number and location follows the standard International 10-20 electrode placement, as shown in FIGS. 3A and 3B. The letters F and T refer to placement on the frontal and temporal lobes of the brain, while the odd numbers refer to the left side of the brain with the even numbers refer to the right side.

The location of a lead on the scalp is also referred to below as a site. The current invention is concerned with an improved treatment protocol that is based on a discovery that improved outcomes for patients are obtained by ordering the treating at each location in accordance with the feedback results as described further below. That is the present invention is primarily concerned with a method of treatment wherein the order of treatment through each such lead 105 in FIG. 3AB is predetermined based on the variation in signal in an initial evaluation period.

FIG. 4A is a flow chart of the treatment method using the apparatus 100 of FIG. 1. The inventive treatment process may first deploys a first diagnostic step 401 of collecting EEG measurements at each electrode site to access the brain activity level at a plurality of the electrode sites, such as the 21 shown in FIGS. 3A and 3B.

Figure 6:
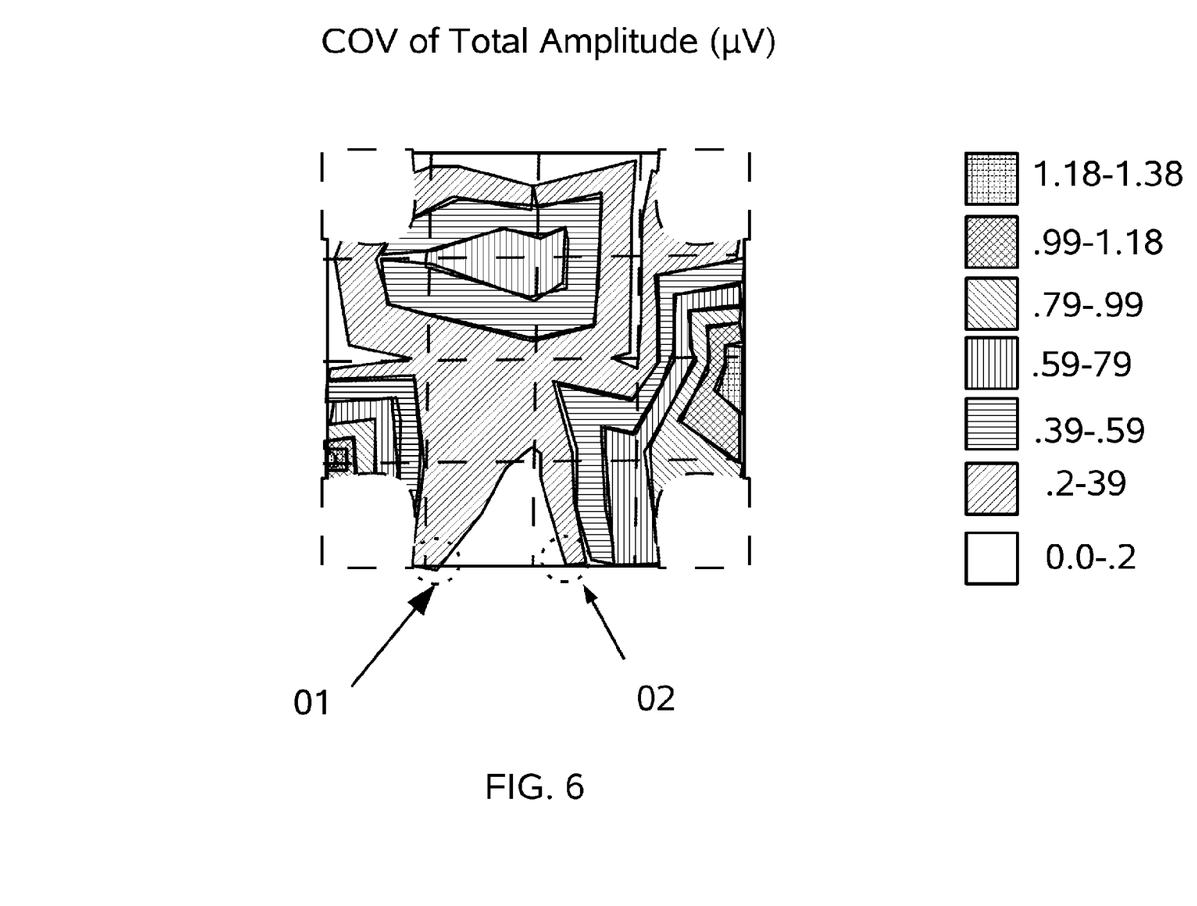
FIG. 6 is a graphic mapping of the COV results illustrating in FIG. 5 to the electrode pattern of FIG. 3B.

In the first step 401 of the treatment process 400, the EEG at each electrode is acquired as a time domain electrical signal. The signal is then digitized and the power spectrum is calculated by a FFT in step 402 to provide the EEG in frequency domain. This EEG data can be acquired for each site used, in sequence. If a map such as shown in FIG. 6 is being created, the sequence is any desired sequence. If data is being acquired in a treatment mode, vs. in a map, or evaluation mode, the sequence is dictated by the sequence predicted by the last map performed, as explained further below.

The collection of EEG signals in step 401 is preferably a continuous measurement every $1/16^{th}$ sec. for a total time of at least about 1 sec to then calculate the FFT (step 402) for each the 16 times segments. However, the measurement can be for longer periods of time, such as two or more seconds. If the measurement is for a longer period of time, each new measurement every $1/16$ of a second can average the past 16 measurements.

In step 403, the Coefficient of Variance (COV) between the 16 FFT's is preferably determined for a plurality of Activity parameters in which the COV is the standard deviation (SD) of the activity parameter value divided by a mean value, such as the mean amplitude. Preferably, there is at least one second of measurement, but more preferably two consecutive seconds of measurement to derive an average COV for any particular site. With less than 1 or 2 seconds in the average for that site, there may be less than sufficient variability at that site from which to extract clinically useful deviations from the mean for calculating the COV.

In step 404 a determination is made if EEG's have been obtained at all or a sufficient number of EEG electrode sites, if not, in step 405, a different electrode is selected for EEG acquisition per step 401.

The COV can be determined for at least 5 different activity parameters from the same 16 or more FFT by considering the deviations in signal character in some portion of the frequency band amplitude or dominant frequency. The dominant frequency is the arithmetic mean of frequency across all values across the entire power spectrum from 0 to 35 Hz, which is δ to β. The Total amplitude, as distinct from the calculation of amplitude for each frequency band, is the simple square root of the power-area under the curve of the entire measured spectrum. Thus, an activity parameter is a characteristic of some predetermined portion or all of the FFT spectrum derived from the actual EEG lead signal variation over time.

Preferably, in step 406 the activity of each of at least 2 of these activity parameter sets is compared for each of the electrode sites to determine the final the treatment order, i.e. which electrode site is treated with feedback before another electrode site.

Figure 4B:
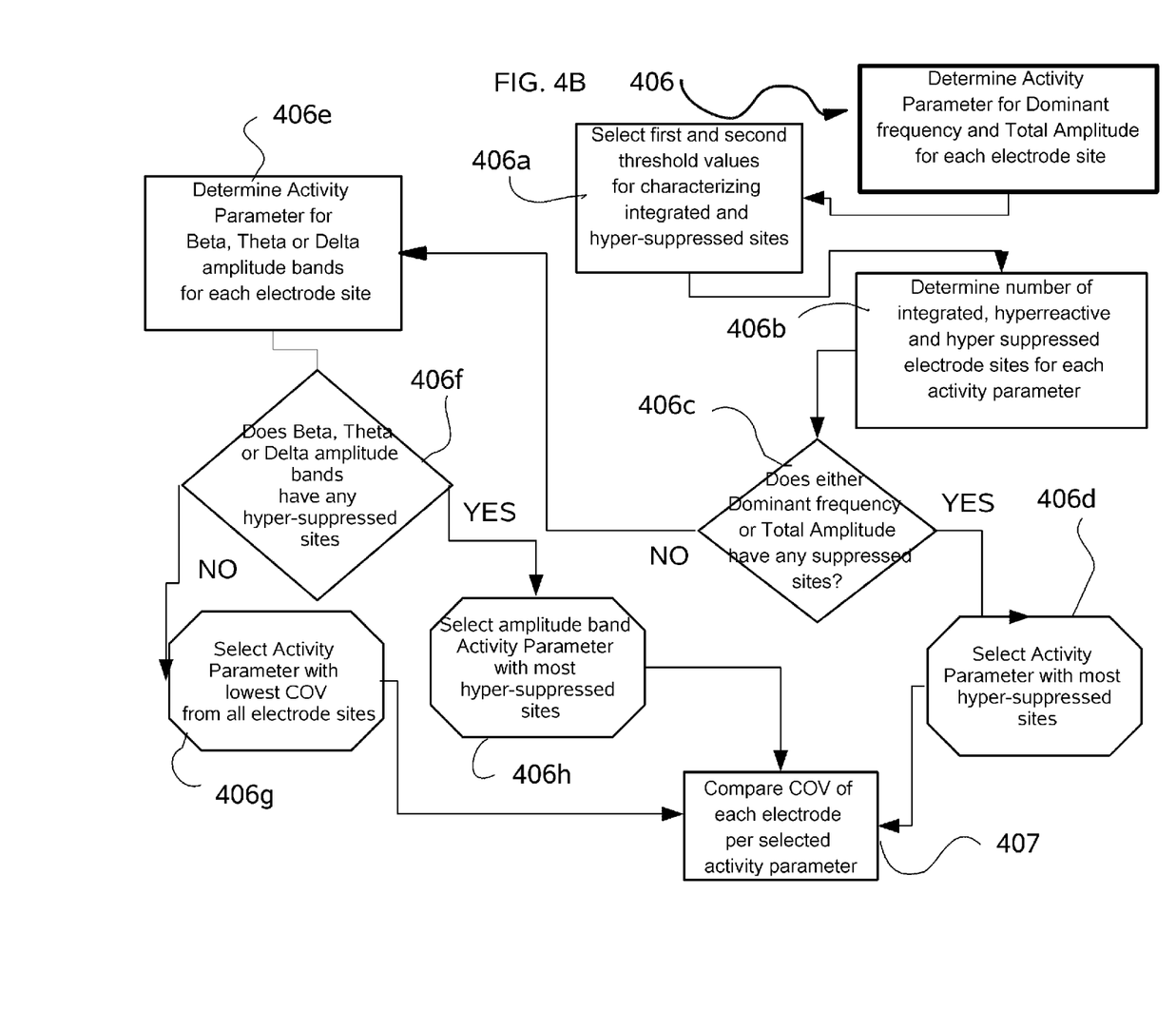
FIG. 4B is a flow chart for a portion of a preferred embodiment of the inventive treatment process that deploys the apparatus of FIG. 1.

FIG. 4B illustrates in a flow chart for step 406 in which the activity parameter used to be used in step 407 for ordering the treatment is selected from among 5 activity parameters.

While this comparison can only takes place after all the desired electrode sites are characterized per step 401, that is the acquisition of the raw signal used to calculate the FFT (step 402), the calculation of the FFT, SD and COV (step 403) can occur as each site is characterized or after all sites are characterized, or any combination thereof. If the electrical activity has not been acquired at all sites, step 401, then the next electrode site is selected per step 405.

It should further be appreciated that depending on the available capacity of the electronics of the apparatus and the analog/digital signal converter (ADSC) or a plurality of contemporaneously operating ADSC's or Digital Signal Processor(s) (DSP), activity at all 21 sites, or some subset thereof, can be obtained simultaneously. Accordingly, FIGS. 4A and 4B, should not be considered as limiting the scope of the invention, but rather as a convenient working example to illustrate the operative principles of the inventive methods, and variations thereof.

In step 406, if all sites have been characterized per step 401 (as decided at step 404) a first selection criterion is used to determine the activity parameter set used in step 407.

Generally speaking, it is preferable to choose the activity parameter set based on the occurrence of the lowest COV values of the electrodes sites.

The activity level can be characterized by the SD of either the amplitude or the dominant frequency, in which the COV is calculated by dividing the SD by the integrated average amplitude. In the case of amplitude, it can be the amplitude of either of the delta, theta and beta ranges, or the amplitude of delta through beta (0-35 Hz), that is at least 4 different activity parameter data sets can be derived for selecting a subset of treatment sites, and determining the order to treat this subset.

In the case of frequency, it is the variation of the dominant frequency from 0 to 35 Hz., providing a $5^{th}$ optional activity parameter data set for selecting a subset of sites for treatment sites.

Thus, by the completion of step 406, each of the electrode sites in the plurality of sites has been characterized by the COV by five different activity parameters, 1) Dominant Frequency, 2) Total band amplitude, or a sub-band amplitude that is alternatively; 3) beta band amplitude, 4) theta band amplitude and 5) delta band amplitude.

The Dominant Frequency, whether the basis for the FFT extraction of the Dominant Frequency is across the entire EEG spectrum or in some special cases, extracted from the frequency band for an particular sub-band such as delta, theta, etc In selecting the activity parameter set to use for step 407, it is first helpful to characterize the activity level at each electrode site into three categories based on their value using the method shown in FIG. 4B. Such characterization requires selecting a first and second threshold for the COV (step 406a). Preferably, sites with a COV greater than a first threshold value of about 0.35 are considered hyperreactive, while sites with a COV of less than a second threshold value of about 0.25 are considered hypersuppressed. Those sites having a COV of between about 0.25 to 0.35 are considered integrated.

Next in step 406b the number of integrated, hyper-active and hyper-suppressed sites can be determined for the primary activity parameters of Dominant Frequency and Total Amplitude. Then in step 406c it is determined if either the Dominant Frequency or the Total Amplitude activity parameter have any hyper-suppressed sites. When this occurs, the activity parameter of the most hyper-suppressed sites is selected (step 406d) for the subsequent comparison of the COV in step 407.

If neither the Dominant Frequency and the Total Amplitude activity parameters has hyper suppressed sites, then further activity parameters can be determined in steps 406e for each electrode site based on the COV for the 3) beta amplitude, 4) theta amplitude and 5) delta amplitude bands. Thus, in step 406f, it is determined in any of the electrode sites exhibit hyper-suppression when characterized by the COV for the sub-band activity parameters: 3) beta amplitude, 4) theta amplitude and 5) delta amplitude bands. Then in step 406f, if any of these sub-band activity parameters has hyper-suppressed sites, then the sub-band activity parameter having the most hyper-suppressed sites is selected for the subsequent comparison of the COV in step 407.

If it is determined in step 406f, that none of the sub-band activity parameters have any hyper-suppressed sites, then the sub-band activity parameter selected for the subsequent comparison of the COV in step 407 is preferably determined in step 406g by summing the COV of all the electrode sites regardless of the characterization in step 406a to select the activity parameter with the lowest COV from all electrode sites.

Alternatively, in step 406h, if none of these sub-band amplitude based activity parameters has any suppressed sites, the section can be based on general level of lower COV or some comparative, normalized or other potential representative portion or all of the electrode sites.

Once the activity parameter is thus selected in step 406, in step 407 at least some, that is either the full set or a subset of these sites, is selected for low energy neurofeedback treatment in step 409.

It is preferable that this subset is the integrated and hyper-sensitive sites, characterized in step 406b, but the number of electrode sites eventually treated, and time between treatments, may be dictated by factors such as sensitivity and vitality of the patient, as is usually judged by the clinician conducting the treatment. Once this subset is selected the order of treatment in step 409 is preferably from highest to lowest COV in the subset.

It should be appreciated that all the site ordering in step 408 may be different depending on the selection of the activity parameter in step 406, as for examples when using COV values for ordering based on either the Total Amplitude and Dominant Frequency. However as long as one is consistent in choice of one or the other, and not mixing the sequences in step 408 based on different activity parameters, there appears to be no practical conflict. Taking direction from a mixture of the two sources of sequences does, however, present conflicts with negative implications for treatment.

Figure 5:
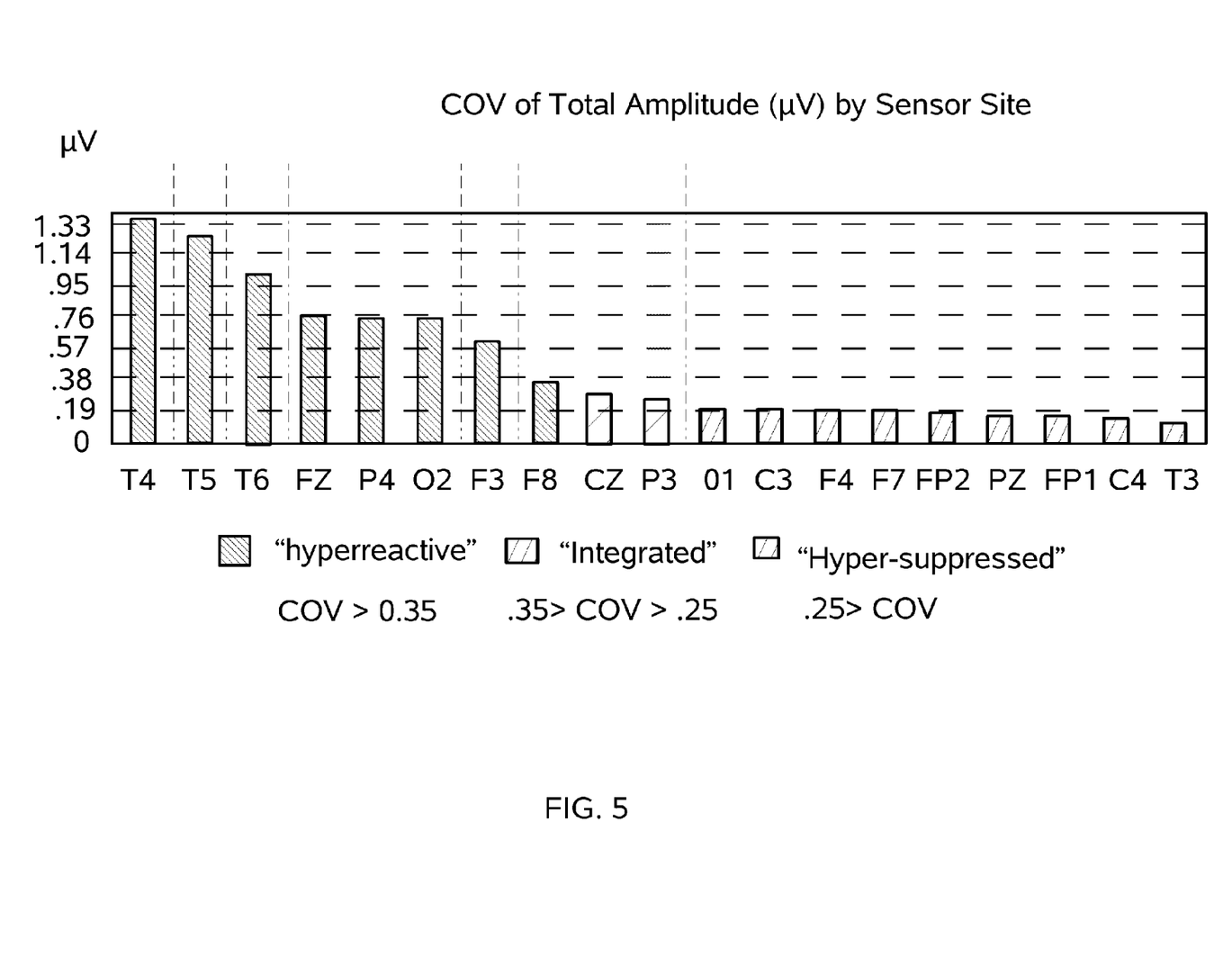
FIG. 5 is a graphic illustration of the result of characterizing a patient with the inventive method wherein the resulting signals from each of the EEG electrodes are ordered by descending COV to highlight the preferred sub-set thereof that are likewise treated in descending order.

FIG. 5 is a bar graph showing the COV of 21 electrode sites sorted by COV from higher to lowest in which each bar has one of three hatching pattern to distinguish hyper-active, integrated and hyper-suppressed sites. FIG. 6 is a graphic display of the COV as a 2-dimensional map of the 21 sites when spatially normalized to a square grid with each intersection of the grid representing a site with the surrounded area hatched per the key at the left side of the diagram, with the Total Amplitude COV in microvolts. The shading between grids is calculated by a linear gradient between grid intersections.

It should be appreciated that as a 2-dimensional plot of 5×5 grid is automatically generated by commercial software (Microsoft Excel™) using 25 data points, the c4 corners of the grid were given null values as only the COV values from the 21 electrodes of the 10-20 configuration of FIGS. 3A and 3B were available. This approximation results in slightly distorting the shape of the regions are the adjacent intersection representing discrete electrodes, the graphics program performing linear 2-dimension interpolations between adjacent grid points to delimit area for different shading patterns. Accordingly, the gradients in the 4 corners of the grid, as well as the zero values in the 4 corners should be ignored and are thus not shown. Thus, the points on this grid align with the electrode matrix in FIG. 4A, with the O2 electrode denoted at the bottom. Electrodes not denoted in the bar graph in FIG. 5 also have a zero or null value when creating the graph In the final step 409 of treatment neurofeedback is provided to the selected sub-set of electrode site in the order of highest to lowest COV for the selected activity parameter. In this the final step 409, neurofeedback is optionally based on the previously dominant frequency at each site as identified from the FFT. Generally, this feedback is very low energy applied at one or more frequencies that are this dominant frequency plus a predetermined offset value which is typically between about 5 and 20 Hz. The treatment time is generally about a second at each electrode site. More preferably, the dominant frequency is recalculated every $\frac{1}{16}^{th}$ of a second, and the treatment frequency updated every $\frac{1}{16}^{th}$ of a second using this refreshed dominant frequency.

In clinical practice the treatment type is selected as appropriate to the patient's conditions and the time of treatment or the number of sites treated in a single therapy session may be extended or reduced depending on the patient sensitivity.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. A method of low energy neurofeedback treatment, the method comprising the steps of:
    a) attaching a plurality of electro-encephalograph (EEG) leads to the head of a patient,
    b) acquiring via an EEG amplification and computing means a baseline EEG at 2 or more leads of said plurality,
    c) calculating a fast Fourier transform (FFT) of the acquired baselines with the computing means for at least 16 time segments to derive one or more activity parameter values,
    d) calculating at least one coefficient of variance (COV) of the one or more activity parameter values from the FFT for each of the 2 or more leads in said plurality,
    e) providing a neurofeedback treatment to the patients via at least some of the each of the 2 or more leads in said plurality, the neurofeedback being provided in the sequence of EEG leads characterized by a higher COV to lower COV.

2. A method of low energy neurofeedback treatment according to claim 1 further comprising the step of calculating a COV for 2 or more activity parameters for each of the 2 or more leads in said plurality, and     a) selecting one of said activity parameters for the purpose of providing the neurofeedback in the order of highest COV to lowest COV of said selected activity parameter.

3. A method of low energy neurofeedback treatment according to claim 2 further comprising the step of:

a) providing a neurofeedback treatment to the patients via at least some of the each of the 2 or more leads in said plurality, the neurofeedback being provided in the sequence of EEG leads characterized by a higher COV to lower COV for the selected activity parameter.

4. A method of low energy neurofeedback treatment according to claim 3 wherein the activity parameter is selected from the group consisting of Dominant Frequency and Total band amplitude.

5. A method of low energy neurofeedback treatment according to claim 4 further comprising the steps of:

a) selecting a first threshold value for defining a first sub-group of EEG leads, wherein the first sub-group has a COV less than the first threshold,     b) selecting a second threshold value for defining a second sub-group of EEG leads, wherein the second sub-group has a COV less than second threshold and greater than or equal to the first threshold,     c) determining for each activity parameter the number of EEG leads in the second sub-group,     d) selecting the activity parameter characterized as having more EEG leads in the second subgroup than any other activity parameter.

6. A method of low energy neurofeedback treatment according to claim 5 wherein the 2 or more leads in said plurality of EEG lead selected for neurofeedback are from the first and second sub-groups.

7. A method of low energy neurofeedback treatment according to claim 1 wherein the two or more activity parameters are selected from the group consisting of Dominant Frequency, Total band amplitude, Beta band amplitude, Theta band amplitude and Delta band amplitude.

8. A method of low energy neurofeedback treatment according to claim 7 further comprising the steps of:

a) selecting a first threshold value for defining a first sub-group of EEG leads, wherein the first sub-group has a COV less than the first threshold,     b) selecting a second threshold value for defining a second sub-group of EEG leads, wherein the second sub-group has a COV less than second threshold and greater than or equal to the first threshold,     c) determining for each activity parameter the number of EEG leads in the second sub-group,     d) selecting the activity parameter characterized as having more EEG leads in the second subgroup than any other activity parameter.

9. A method of low energy neurofeedback treatment according to claim 8 wherein the first threshold value is 0.25 microvolts and the second threshold value is 0.35 microvolts.

10. A method of low energy neurofeedback treatment according to claim 1 wherein the neurofeedback comprises providing a low energy signal to each EEG lead at a frequency that is the dominant frequency for the EEG lead plus a predetermined offset.

11. A non-transient computer readable medium having a computer program instructions stored thereon which, when executed by a computer, performs the steps in the methods as claimed in claim 4.

12. An apparatus for low energy neurofeedback treatment, the apparatus comprising:

a) a plurality of EEG leads for attachment to the patient,     b) an EEG amplifier in signal communication with said EEG leads, the EEG amplifier consisting essentially of means to amplify signal received from the leads attached to the patient,     c) a computer in signal communication with said EEG amplifier to acquire and display the EEG,     d) at least one of the EEG amplifier and computer comprising computational means to determine the dominant frequency in each EEG lead pair,     e) wherein the computer is operative to performs the steps in the methods as claimed in claim 5.

13. A non-transient computer readable medium having a computer program instructions stored thereon which, when executed by a computer, performs the steps in the methods as claimed in claim 9.

14. A method to provide data for low energy neurofeedback treatment, the method comprising the steps of:

a) attaching a plurality of electro-encephalograph (EEG) leads to the head of a the patient,     b) acquiring via an EEG amplification and computing means a baseline EEG at 2 or more leads of said plurality,     c) calculating a fast Fourier transform (FFT) of the acquired baselines with the computing means for a plurality of time segments to derive one or more activity parameter values,     d) calculating at least one coefficient of variance (COV) of the one or more activity parameter values from the FFT for each of the 2 or more leads in said plurality,     e) characterizing the one or more activity parameter values in a sequence of EEG leads used to calculate the COV in step (d) in the order of COV value level.

15. A method to provide data for low energy neurofeedback treatment according to claim 14, the method further comprising the step of calculating a COV for 2 or more activity parameters for each of the 2 or more leads in said plurality, and     a) selecting one of said activity parameters for the purpose of providing the neurofeedback in the order of highest COV to lowest COV of said selected activity parameter.

16. A method to provide data for low energy neurofeedback treatment according to claim 14 wherein the activity parameter is selected from the group consisting of Dominant Frequency and Total band amplitude.

17. A method to provide data for low energy neurofeedback treatment according to claim 14 wherein the two or more activity parameters are selected from the group consisting of Dominant Frequency, Total band amplitude, Beta band amplitude, Theta band amplitude and Delta band amplitude.

18. A method to provide data for low energy neurofeedback treatment according to claim 14 further comprising the steps of:

a) selecting a first threshold value for defining a first sub-group of EEG leads, wherein the first sub-group has a COV less than the first threshold,     b) selecting a second threshold value for defining a second sub-group of EEG leads, wherein the second sub-group has a COV less than second threshold and greater than or equal to the first threshold, c) determining for each activity parameter the number of EEG leads in the second sub-group, d) selecting the activity parameter characterized as having more EEG leads in the second subgroup than any other activity parameter.

19. A method to provide data for of low energy neurofeedback treatment according to claim 18 wherein the 2 or more leads in said plurality of EEG lead selected for neurofeedback are from the first and second sub-groups.

20. A method to provide data for of low energy neurofeedback treatment according to claim 18 wherein the first threshold value is 0.25 microvolts and the second threshold value is 0.35 microvolts.

* * * * *